(12) United States Patent
Paulsen et al.

(10) Patent No.: US 7,399,496 B2
(45) Date of Patent: Jul. 15, 2008

(54) HYDROLYZED WHEY PROTEIN COMPOSITIONS

(75) Inventors: Starla Paulsen, Twin Falls, ID (US); Loren Spencer Ward, Twin Falls, ID (US); Eric Douglas Bastian, Twin Falls, ID (US); Brent Petersen, Twin Falls, ID (US); Bonney Oommen, Twin Falls, ID (US)

(73) Assignee: Glanbia Nutritionals (Ireland) Limited, Kilkenny (IE)

( * ) Notice: Subject to any disclaimer, the term of this patent is extended or adjusted under 35 U.S.C. 154(b) by 0 days.

(21) Appl. No.: 10/702,758

(22) Filed: Nov. 6, 2003

(65) Prior Publication Data

US 2004/0156969 A1    Aug. 12, 2004

Related U.S. Application Data

(60) Provisional application No. 60/486,356, filed on Jul. 11, 2003, provisional application No. 60/445,750, filed on Feb. 7, 2003.

(51) Int. Cl.
    *A23J 1/20*    (2006.01)
(52) U.S. Cl. ............... 426/657; 426/583; 426/656
(58) Field of Classification Search ............... 426/656, 426/583
    See application file for complete search history.

(56) References Cited

U.S. PATENT DOCUMENTS

| 4,107,334 | A | * | 8/1978 | Jolly .............................. 426/7 |
| 4,427,658 | A | * | 1/1984 | Maubois et al. ................ 514/2 |
| 4,748,034 | A |   | 5/1988 | de Rham |
| 4,847,096 | A | * | 7/1989 | Mellqvist et al. ............. 426/41 |
| 5,112,812 | A |   | 5/1992 | Samuelsson et al. |
| 5,589,357 | A | * | 12/1996 | Martinez et al. ........... 435/68.1 |
| 5,691,165 | A |   | 11/1997 | Nielsen et al. |
| 5,780,439 | A | * | 7/1998 | Mendy et al. ................. 514/21 |
| 5,882,705 | A | * | 3/1999 | Sato et al. ..................... 426/41 |

(Continued)

FOREIGN PATENT DOCUMENTS

EP    0 269 593    6/1988

(Continued)

OTHER PUBLICATIONS

Moringa Milk Ind Co. Ltd., Database WPI. Section CH, Week 200305. Derwent Publications Ltd., London, GB: AN 2003-049445. XP002287317 & JP 2002 238462 A. (Aug. 27, 2002) abstract.

(Continued)

*Primary Examiner*—Anthony Weier
(74) *Attorney, Agent, or Firm*—Banner & Witcoff, Ltd.

(57) ABSTRACT

The present invention relates to whey protein compositions that can be incorporated into solid foodstuffs and liquid compositions to provide supplemental amounts of protein. The foodstuffs and liquid compositions are stable when subject to conditions of heat and/or time and can include increased amounts of whey proteins. Methods of making the compositions include providing a protein solution including an enzyme for providing a predetermined degree of hydrolysis of the protein solution, maintaining the temperature and pH of the solution to hydrolyze the protein solution and providing an essentially neutral whey protein hydrolysate, and separating the protein solution using a membrane filtration process to obtain a retentate of whey protein hydrolysate having an essentially neutral pH.

7 Claims, 4 Drawing Sheets

U.S. PATENT DOCUMENTS

| | | | |
|---|---|---|---|
| 6,060,269 | A | 5/2000 | Chatterton et al. |
| 6,261,624 | B1 * | 7/2001 | Hudson et al. .............. 426/573 |
| 6,455,273 | B1 | 9/2002 | Kodera et al. |
| 6,887,850 | B2 * | 5/2005 | Fuchs et al. .................... 514/2 |
| 6,919,314 | B1 * | 7/2005 | Schlothauer et al. .......... 514/13 |
| 2002/0012720 | A1 | 1/2002 | Chen |

FOREIGN PATENT DOCUMENTS

| | | |
|---|---|---|
| GB | 2 335 134 | 9/1999 |
| WO | WO 02/19837 | 3/2002 |

OTHER PUBLICATIONS

Nochinko Sangyo Shinko Jigyodan, Database WPI. Section CH, Week 199816. Derwent Publications Ltd., London, GB: AN 1998-172040. XP002287318 & JP 10 033115. (Feb. 10, 1998) abstract.

International Search Report mailed Jul. 19, 1004.

Best, Dan, "Protein Wars—Command and Conquer. Oh, How the Natural Products Expo Has Changed", Stagnito's New Products Magazine, vol. 2, No. 5, p. 46(2), May 2002, United States.

Gallo-Torres, Julia M., "Raising the Bar", Prepared Foods, vol. 171, No. 9, p. 65(1), Sep. 2002, United States.

LUNA protein bar, Orange Bliss flavor, manufactured by Clif Bar Inc., Berkeley California, no date provided.

Harvest, Whole Grain Energy Bar, Carrot Cake flavor, manufactured by PowerBar, Inc., Berkeley California, no date provided.

Balance +, Food Bar, Lemon Meringue flavor, manufactured by balance Bar Company, Rye Brook, New York, no date provided.

Power Crunch, High Protein Energy Snack, Peanut Butter Crème flavor, manufactured by BioNutritional Research Group, Santa Ana Hts. California, no date provided.

Steel Bar, protein bar, Chocolate Crisp flavor. manufactured by American Body Building Products, LLC, Walterboro, South Carolina, no date provided.

Protein 2 Go, High Energy Protein Bar, Fudgy Peanut Butter Cup flavor, manufactured by Interactive Nutrition International, Inc., Ottawa ON Canada, no date provided.

Advantage, low carbohydrate bar, Chocolate Peanut Butter Bar, distributed by Atkins Nutritionals, Inc., Ronkonkoma, New York, no date provided.

Odyssey, Triple Layer Protein Bar, Chocolate Coconut Almond flavor manufactured by Prepier Nutrition, Inc., Carlsbad California, no date provided.

Designer Whey, Gourmet Bar, Chocolate Triplement flavor, manufactured by Next Proteins International, Carlsbad California, no date provided.

Meso-Tech, Meal-Replacement Energy Bar, Wild Berry Crisp flavor, product of Canada, manufactured for Muscle Tech R&D, Inc., Mississauga, ON, Canada, no date provided.

Procrunch, Protein Nutrition Bar, Chocolate Crisp flavor, distributed by General Nutrition Corp., Pittsburgh, PA, no date provided.

Odyssey, Triple Layer Protein Bar, Caramel Nut flavor, manufactured by Premier Nutrition, Carlsbad, California, no date provided.

Ensure, Nutrition and Energy Bar, Chewy Chocolate Peanut flavor, distributed by Ross Products Division, Abbott Laboratories, Inc., Columbus Ohio, no date provided.

Café Creations, A Sweet Indulgetn Pastry Bar, Cinnamon Danish flavor, manufactured and distributed by Health Valley Company, a division of the Hain Celestial Group, Inc., Irwindale, California, no date provided.

Bumble Bar, Organic Energy, Lushus Lemon flavor, manufactured by Bumble Bee Inc. Vashon, WA, no date provided.

Monster Oatmeal Cookie, manufactured by Mrs. Denson's Cookie Co., Inc., Ukiah California, no date provided.

Oasis, Complete Nutrition Bar for Women, Strawberry Cheesecake flavor, distributed by Balance Bar Company, Rye Brook, New York, no date provided.

Peanut Butter Cookie, manufactured by Alternative Baking Company, Inc., no date provided.

Genisoy, Delicious Soy Protein Bar, Southern Style Chunky Peanut Butter Fudge flavor, manufactured by GeniSoy Products Co., Fairfield California, no date provided.

Centrum Performance Energy, Nutrition Bar, Chocolate Nougat flavor, marketed by Whitehall-Robins Healthcare, Madison New Jersey, no date provided.

Spiru-Tein, High Protein Energy Meal, Chocolate Peanut Butter Swirl flavor, manufactured by Nature's Plus, Melville, New York, no date provided.

Kashi Go Lean, High Protein/High Fiber Bar, Oatmeal Raisin Cookie flavor, distributed by Kashi Company, La Jolia, California, no date provided.

Kashi Go Lean, High Protein/Fiber Bar, Honey Vanilla Yogurt flavor, distributed by Kashi Company, La Jolla California, no date provided.

Advant EDGE Carb Control Nutrition Bar, Blueberry flavor, manufactured by EAS, Inc., Golden, Colorado, no date provided.

Animal Parade, Kid's Nutrition Bar, Peanut Butter & Jelly flavor, manufactured by Nature's Plus, Melville, New York, no date provided.

Results for Women, Complete Energy Bar, Amazing CranApple flavor, manufactured by,EAS, Inc., Golden Colorado, no date provided.

Genisoy, Delicious Soy Protein Bar, Fair Trade Arabica Café Mocha Fudge flavor, manufactured by GeniSoy Products, Co., Fairfield, California, no date provided.

Opti-Pro Meal, High Protein Nutrition Bar, Key Lime Pie flavor, manufactured by Optimum Nutrition, Coral Springs Florida, no date provided.

Power Crunch, High Protein Energy Snack, Peanut Butter Fudge flavor, manufactured by BioNutritional Research Group, Santa Ana Hts., California, no date provided.

MET-Rx Protein Plus, High Protein Food Bar, Chocolate Fudge flavor, manufactured by MET-Rx, Boca Raton, Florida, no date provided.

Meso-Tech, protein bar, Peanut Butter Chocolate flavor, manufactured by Muscle Tech Research and Development, Inc., Brampton ON Canada, no date provided.

Pure De-lite, High Protein Cookie, Peanut Butter Chew flavor, Distributed by PureDe-Lite products, Inc., Provo Utah, no date provided.

Kashi Go Lean, High Protein/High Fiber Bar, Mocha Java flavor, distributed by Kashi Company, La Jolia California, no date provided.

LUNA protein bar, Chocolate Peppermint Stick flavor, manufactured by Clif Bar Inc., Berkeley California, no date provided.

Southern Delite, Protein Brownie Bar, Chocolate-Coated Peanut Butter flavor, sugar free, manufactured by Southern Signature Foods, Inc., Boone, North Carolina, no date provided.

Metabolift, Thermogenic High Protein, Low Carb Diet Bar, Lemon Delite flavor, distributed by Twin Laboratories, Inc., Ronkonkoma, New York, no date provided.

GeniSoy, Delicious Soy Protein Bar, Ultimate Chocolate Fudge Brownie flavor, manufactured by GeniSoy Products, Co., Fairfield, California, no date provided.

Snacbar, nutrition bar, Chocolate flavor, manufactured by Champion Nutrition, Concord, California, no date provided.

Protein Fort, High Protein Bar, Orange flavor, made in Argentina, no date provided.

Spiru-Tein, High Protein Energy Meal, Original flavor, manufactured by Nature's Plus, Melville, New York, no date provided.

Dr. Soy, Soy Protein Bar, Chocolate Peanut flavor, manufactured by DrSoy Nutrition, LLC, Irvine, California, no date provided.

Slim-Fast, Meal Bar, Apple Cobbler flavor, distributed by slim-Fast Foods Co., West Palm Beach, Florida, no date provided.

Protein Plus, protein bar, Chocolate Chip flavor, manufactured for Carbolite Foods, Inc., Evansville, Indiana, no date provided.

Protein Plus, High Protein Bar, Vanilla Yogurt flavor, manufactured by Powerbar, Inc., Berkeley California, no date provided.

Ultimate Protein, Candy chocolate pieces, manufactured for Biochem, Pauppauge, New York, no date provided.

Opti-Pro Meal, High Protein Nutrition Bar, Peanut Butter Crunch flavor, manufactured by Optimum Nutrition, Coral Springs, Florida, no date provided.

Cereal Fort, cereal bar, made in Argentina, no date provided.

Pure Protein, High Protein Bar, Peanut Butter flavor, manufactured for Worldwide Sport Nutritional Supplements, Inc., Boca Raton, Florida, no date provided.

Advant Edge, Complete Nutrition Energy Bar, Iced Oatmeal Raisin Crisp flavor, manufactured for EAS, Inc., Golden Colorado, no date provided.

Pemmican, Concentrated Food Bar, Fruit & Nut flavor, manufactured by latermountain Trading Co., Ltd., Albany, California, no date provided.

Balance Gold, Triple Layer Energy Bar, Rocky Road flavor, distributed by Balance Bar Company, Rye Brook, New York, no date provided.

Health Valley Granola Bar, Peanut crunch flavor, made by Health Valley Company, Irwindale, California, no date provided.

Nutribar, Meal Replacement Bar & Weight Loss Plan, Deep Brownie Delight flavor, distributed by Stella Pharmaceutical Company, Dayton, New Jersey, product of Canada, no date provided.

Clif Bar, protein bar, Crunchy Peanut Butter flavor, manufactured by Clif Bar Inc., Berkeley California, no date provided.

Bioprotein, protein bar, chocolate peanut butter flavor, manufactured by MLO Products, Inc., Fairfield, California, no date provided.

Metabolift, Thermogenic High Protein, Low Carb Diet Bar, Chocolate Mint flavor, distributed by Twin Laboratories, Inc., Ronkonkoma, New York, product of Canada, no date provided.

Advantage, low carbohydrate bar, Creamy Berry Cheesecake flavor, distributed by Atkins Nutritionals, Inc., Ronkonkoma, New York, no date provided.

* cited by examiner

—o— Whey Protein Blend 50:50
–◻– Unhydrolyzed Whey

—o— Whey Protein Blend 70:30
–◻– Unhydrolyzed whey

HYDROLYZED WHEY PROTEIN COMPOSITIONS

CROSS REFERENCE TO RELATED APPLICATIONS

This application is based on, and claims the benefit of U.S. Provisional Application Ser. No. 60/486,356, filed on Jul. 11, 2003 and U.S. Provisional Application Ser. No. 60/445,750, filed Feb. 7, 2003, the disclosures of which are incorporated herein by reference.

FIELD OF THE INVENTION

The present invention relates to compositions including whey proteins that are suitable for preparation of temperature and shelf-stable nutritional products, methods for making such compositions and nutritional products. The compositions allow incorporation of whey proteins in amounts up to 100% of the protein source of the temperature and shelf-stable nutritional products.

BACKGROUND OF THE INVENTION

Food products to provide supplemental amounts of nutritional components to a consumer have become increasingly popular in recent years. Both solid food items and beverages are available that provide desired nutritional components to individuals who seek nutritional supplements as a result of diet or activity level. For example, various beverages and snacks have been suggested to address the nutritional needs of children or athletes. Nutritional bars can deliver relatively high levels of nutritional ingredients in a single serving size. Beverages also can be used to quickly deliver the desired nutritional components.

Protein is one nutritional component that often is sought in dietary supplements. Among the numerous sources of protein, whey proteins have a high nutritive value, due in part at least to the compositional profile of the proteins that includes a balanced array of amino acids. As a result, whey proteins are recognized as a premier protein source, particularly for individuals who are health-conscious and have specific dietary needs, such as athletes and body builders. Generally, it is desired to provide as much protein as possible from whey proteins.

Various problems associated with incorporation of proteins, particularly whey proteins, have prevented their successful use as the sole source of protein in food products, such as nutritional supplement bars and beverages. For example, although a protein bar that includes 100% of protein from whey protein may initially have acceptable flavor and texture characteristics, these characteristics will rapidly decline, within a matter of weeks even, so that the bar is no longer appealing to the consumer. In particular, an overall hardening of the bar results in decreased shelf life and a generally unacceptable food product. Such a protein bar is no longer suitable for commercial sale and consumption. These problems also have prevented preparation of food products having higher levels of whey proteins, such as greater than about 25 weight percent protein. To overcome these problems, food products such as protein bars typically include a blend of protein sources, including but not limited to whey proteins, milk proteins, wheat proteins, calcium caseinate, skim milk, soy proteins and others to achieve a soft food product having a longer shelf life.

Nutritional liquid compositions or beverages, such as sports nutrition beverages, also suffer from problems as the protein fraction from whey protein is increased. Drinks are available that contain only whey proteins, however, such drinks are acidic (pH less than 4.5) in order to provide a stable food product. As a result of the high acidity, their flavor may be unappealing to consumers. Additionally, the beverages typically are clear liquids so that appearance can be a concern.

Efforts to provide a neutral pH beverage, and thus limit the acidic "bite" associated with nutrition beverages, while maintaining whey protein as the only protein source have been difficult at best. As the pH of a whey protein beverage is increased, the ability of the beverage to withstand heat treatment decreases and the physical properties of the beverage tend to become unstable. For example, attempts to use whey protein as the sole protein source in a neutral pH beverage that delivers supplemental amounts of protein have been unsuccessful. Whey proteins become cloudy and/or precipitate when subjected to elevated temperatures, such as during pasteurization, which is typically a required processing step. Thus, other less-desirable forms of protein, including but not limited to caseinates and soy proteins, have been used in addition to, or instead of, whey proteins to deliver the desired amount of protein to the consumer while providing a stable beverage product.

There remains a need for compositions that allow incorporation of whey proteins as the primary or even sole protein source and that can be used to prepare food products of desired taste and texture. There also remains a need for food products that deliver supplemental amounts of nutritional components such as protein and that remain stable when subjected to conditions including heat and time.

SUMMARY OF THE INVENTION

The present compositions and methods overcome the difficulties previously encountered during manufacture of food products where incorporation of an increased amount of whey proteins into the food products such as nutritional supplement products has resulted in an accelerated decline in the quality of the physical properties of the food products. The compositions and methods provide enhanced levels of nutritional components including proteins, and more particularly whey proteins. In one aspect of the invention, solid food products having increased amounts of whey protein based on the weight of the food product can be prepared. Generally, food products in accordance with the present invention are stable when exposed to conditions of increased temperature and/or time.

In one aspect, the compositions include hydrolyzed whey proteins. The compositions can be incorporated into foodstuffs to provide a finished food product having desired organoleptic and physical properties for a predetermined period of time. The finished food products have excellent texture and elasticity while delivering enhanced levels of proteins. The compositions can be used to prepare food products that have an extended shelf life. For example, when incorporated into solid food products, the finished food products will maintain a desired softness in texture for a predetermined period of time. The whey protein compositions also may include unhydrolyzed whey protein as needed to adjust the consistency of the food product during preparation to facilitate processing of the food product by mechanical methods including extrusion.

The compositions also can be incorporated into liquids to provide beverages and other liquid food products that do not become cloudy and/or precipitate upon heating to temperatures of at least about 180° F. The whey protein compositions can be used to prepare liquid compositions enhanced with whey proteins and having a pH of at least about 5, and even about 6 to about 8, while still providing a heat stable liquid composition. Adjustments to pH need not be made to maintain or enhance the heat stability of the liquid compositions.

The whey protein compositions may be prepared from a whey protein material that has been hydrated to provide a whey protein solution. An enzyme may be mixed with the whey protein solution to hydrolyze the whey protein solution. The solution and enzyme are maintained at a temperature and pH effective for hydrolyzing the whey protein solution while providing an essentially neutral pH whey protein hydrolysate. After hydrolysis has proceeded to the desired degree, the enzyme is inactivated. The solution is filtered using a membrane filtration process, such as nanofiltration, to obtain a retentate comprising whey protein hydrolysate having an essentially neutral pH.

DETAILED DESCRIPTION OF THE INVENTION

Figure 1:
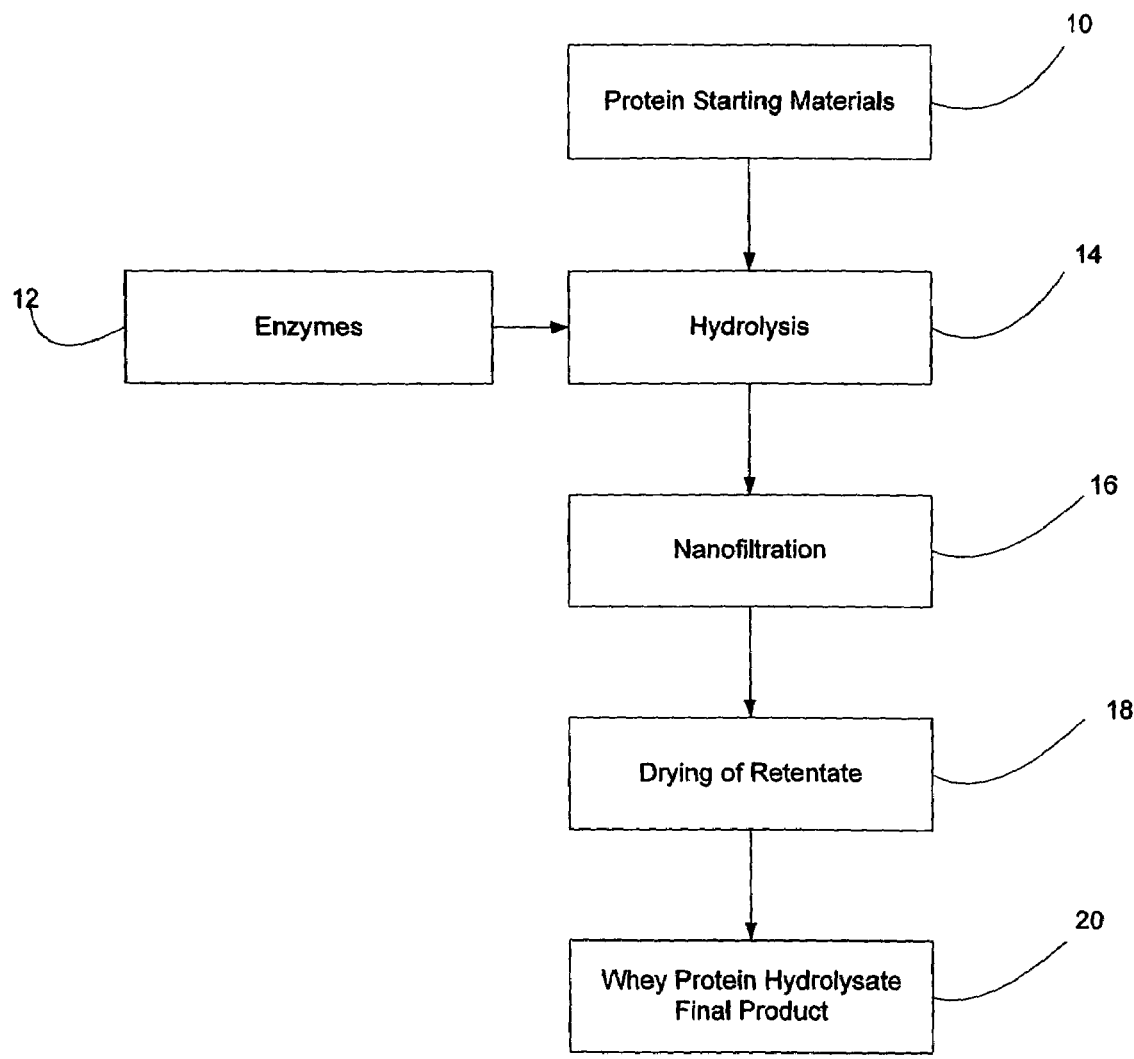
FIG. 1 is a block flow diagram showing a process for preparing a whey protein composition in accordance with the present invention.

The present invention relates to compositions that allow incorporation of whey proteins as the primary or only source of protein in a food product. The whey protein compositions can be used to prepare food products, such as beverages, bars and snacks, having desired organoleptic and functional characteristics. The compositions also can be used to prepare food products having increased protein content, such as 30% or more. Methods of making the whey protein compositions and the food products also are provided. The compositions provide stable products having increased whey protein content without adversely affecting the organoleptic and functional properties of the finished food products.

As used herein, "whey protein hydrolysates" and "hydrolyzed whey proteins" are intended to be used interchangeably and to mean whey proteins that have been hydrolyzed by enzymes, including by any process for hydrolysis of proteins known to those of skill in the art.

As used herein, "shelf life" is intended to refer to the period during which the functional properties of the food product, such as softness and texture, remain acceptable to a consumer and the food product is commercially viable.

The whey protein compositions of the present invention include whey protein hydrolysates. The whey protein hydrolysates can be obtained from hydrolysis of whey, whey protein isolates, whey protein concentrates, and the like, and combinations thereof. The whey proteins can be prepared using any method of hydrolyzing whey proteins known to those of skill in the art. The compositions can be incorporated into a variety of food products, including nutritionally enhanced supplements and snacks like bars, cookies and beverages, to deliver proteins to the consumer. Such food products may be consumed by athletes and/or individuals seeking an energy boost and include sports bars and drinks, along with energy bars and drinks. The whey protein compositions can be incorporated into the product to provide up to 100% of the protein in the product. The whey protein compositions also may enhance the organoleptic and functional characteristics of the food product into which they are incorporated.

Without wishing to be bound by any theories, it is believed that hydrolyzation of whey proteins creates peptide fragments that do not absorb water in the same manner as unhydrolyzed whey proteins. Moisture is retained in the food product for a longer period of time resulting in a food product having a softer texture and an extended shelf life. Thus, it is possible to incorporate hydrolyzed whey proteins in accordance with the present invention into food products to provide a finished food product that has a longer shelf life than that of a food product that does not include hydrolyzed whey proteins.

The whey protein compositions including whey protein hydrolysates also may include whey proteins that have not been hydrolyzed while still providing up to 100% whey protein as the source of protein. Other unhydrolyzed whey proteins, such as whey, whey protein isolates, whey protein concentrates, and the like, and combinations thereof, may be used in combination with the hydrolyzed whey proteins as needed to enhance the consistency of solid food products during preparation of the food product and thereafter. For example, if the consistency of the food product is too soft, unhydrolyzed whey proteins can be incorporated to enhance the texture of the food product and facilitate mechanical processing, including extrusion. In one aspect, the amount of unhydrolyzed whey protein included in the whey protein compositions may be up to about 50 weight percent, and preferably between about 20 to about 50 weight percent, more preferably about 20 to about 35 weight percent, based on the weight of the whey protein composition to provide the desired modifications to the functional properties of the food product. Depending on the formulation of the food product being prepared, the whey protein compositions also can include more than 50 weight percent unhydrolyzed whey proteins as needed, and such whey protein compositions also are contemplated as being within the scope of the invention.

Generally, the amount of whey protein composition that can be incorporated into a food product, as well as the types and relative amounts of whey proteins that are included in the composition, depends at least in part on the overall formulation of the finished food product. The total amount of whey protein composition, as well as the relative amounts of hydrolyzed and unhydrolyzed whey proteins, can be adjusted to provide a finished food product having desired functional properties and nutritional content, taking into account the types and amounts of other ingredients used in the food product. Additionally, other non-whey sources of protein also can be incorporated into the food products if needed to provide desired functional properties or other characteristics of the food product.

Food products prepared using the whey protein compositions can be used to deliver supplemental amounts of protein to the consumer. With a whey protein composition that includes hydrolyzed whey proteins, food products that include a protein component comprising enhanced amounts of whey protein are possible. In one aspect, the whey protein compositions comprise about 50 weight percent or more of the total protein component that is included in the food products. In another aspect, food products having a whey protein composition content of at least about 30 weight percent or more based on the weight of the food product can be prepared. Preferably, food products having a whey protein composition content of at least about 40 weight percent, and more preferably at least about 45 weight percent or more, based on the weight of the food product, can be prepared with the whey protein compositions. As the protein content of the food product increases, the formulation for the food product can be adjusted. For example, the types and amounts of other ingredients such as syrups can be adjusted to facilitate mechanical processing of the food product and account for possible changes to the functional properties of the food product such as thickening in consistency and hardening of texture.

The whey protein compositions can be utilized as a primary or even sole protein source in preparing farinaceous food products, such as bars, biscuits, cookies and other bakery goods. Products made in accordance with the present invention exhibit enhanced shelf stability and maintain desired softness and texture characteristics for at least a predetermined period of time. The products of the present invention also will have low bitterness and a generally appealing flavor.

The whey protein compositions also can be utilized in liquid compositions, such as acidic and neutral pH beverages, as the primary or even sole source of protein. In one aspect of the invention, the pH of the liquid compositions is at least about 5 and preferably between about 6 to about 8, and even between about 6.5 to about 7.5. Liquid compositions made with the whey protein compositions are heat stable, e.g., the proteins remain in solution and the liquid compositions generally do not become cloudy. The liquid compositions can be heated to temperatures required for processing, such as pasteurization, and can be heated to temperatures of at least about 180° F. or more, while remaining stable. The liquid compositions also remain shelf stable for a predetermined length of time. In one aspect of the invention, the whey protein compositions are incorporated into liquid compositions in amounts to provide liquid compositions having about 5 weight percent, more preferably about 10 weight percent, or more whey protein based on the weight of the compositions.

As illustrated in FIG. 1, the present invention includes methods for preparing whey protein hydrolysates. Generally, the methods include mixing a protein starting material 10 with an enzyme or enzyme blend 12 in a hydrolysis tank 14 for a time and at a temperature effective for hydrolyzing the protein starting material. The hydrolyzed protein is nanofiltered 16 under predetermined conditions of temperature and pressure to allow removal of undesirable components, including small peptides and minerals. The retentate from nanofiltration then is spray dried 18 to yield a final whey protein hydrolysate 20.

The starting materials may be any suitable whey material, preferably having at least about 10% protein by weight, more preferably about 50% to about 100% protein by weight, and even more preferably about 80% to about 100% protein by weight, in order to maximize the amount of whey protein provided. In one aspect of the invention, the starting materials include whey, whey protein isolates or whey protein concentrates, and combinations thereof. Preferred starting materials include the whey protein powders sold under the trade names Provon® 190 and 290, which are commercially available from Glanbia Nutritionals, Inc. of Twin Falls, Id.

If the protein starting material is provided in powder form, it can be hydrated with water. A predetermined amount of water can be used to provide a suspension having a desired solids content. The solids content of the protein starting material in solution may be between about 15 to about 25%, based on the weight of the solution.

Figure 2:
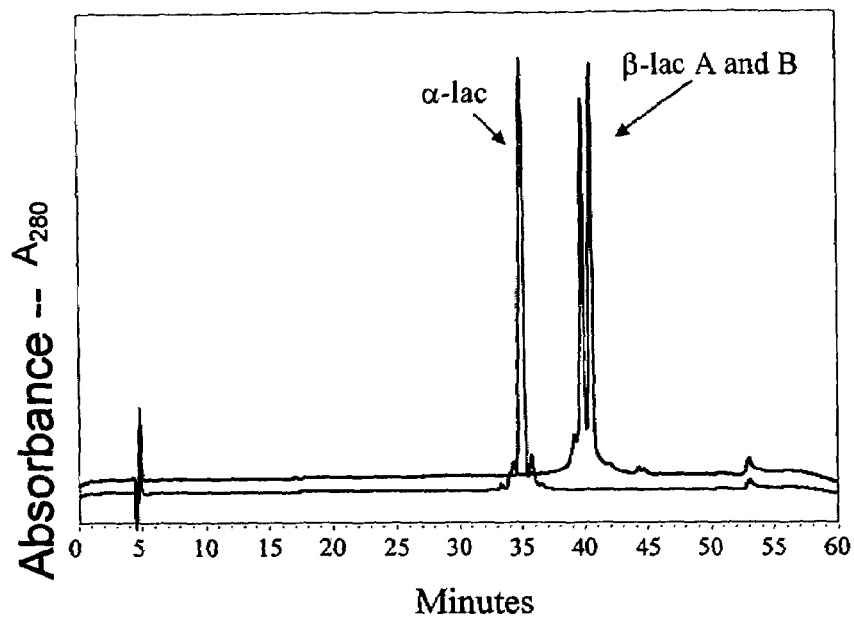
FIG. 2 is a chromatogram that illustrates the composition of a conventional whey protein product.
Figure 3:
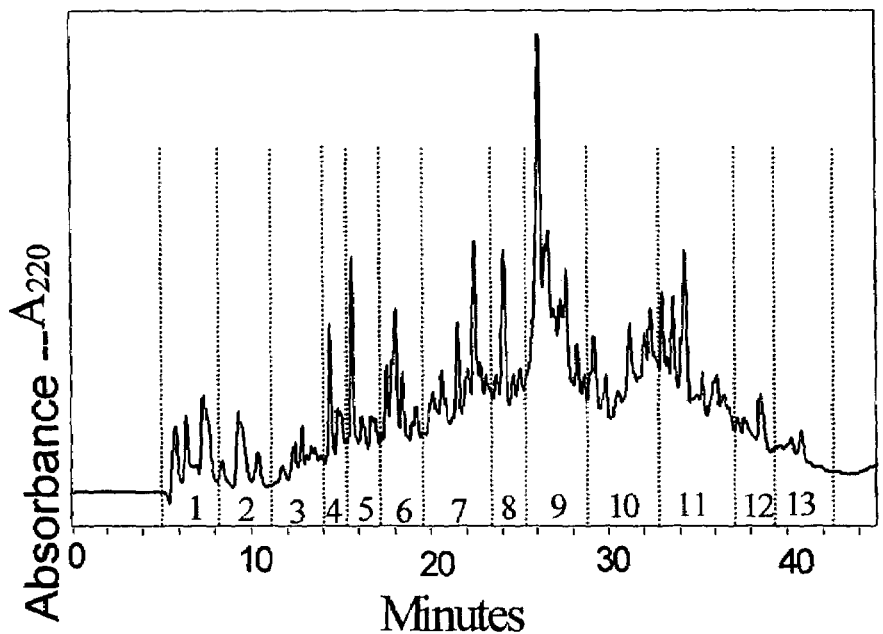
FIG. 3 is a chromatogram that illustrates the composition of a whey protein product prepared in accordance with the present invention.

FIGS. 2 and 3, which are high performance liquid chromatograms (HPLC) obtained using a Waters 2695 instrument, illustrate the typical composition of whey protein before and after hydrolysis. As illustrated in FIG. 2, two primary components of whey protein are alpha-lactalbumin ("α-lac") and beta-lactoglobulin ("β-lac A and B"), which are represented by the two spikes in the figure. As illustrated in FIG. 3, upon hydrolysis, the proteins are converted to a variety peptides, which are represented by the numerous spikes in the figure.

Enzymes used to hydrolyze the whey proteins preferably will have the ability to provide a hydrolyzed product having low bitterness. Preferably, the enzymes are proteolytic enzymes, such as papain, bromolain, trypsin, and pepsin. In one aspect, the enzymes include Debitrase® HYW20, which is commercially available from Rhodia Foods of Madison, Wis., although other enzymes or blend also may be used.

The weight ratio of protein material and enzymes may vary with the materials used. By way of example, when a whey protein material having between about 50 to about 100% protein is used with the enzyme Debitrase® HYW20, the enzyme is added in an amount between about 0.25 to about 2 pounds per 100 pounds of protein. In other aspects, lower amounts of enzyme also may be used with longer hydrolysis times to provide the same final product.

The protein and enzyme solution can be hydrolyzed using any standard equipment known to those of skill in the art. In a hydrolysis tank, the protein solution is held at a time and for a temperature effective for achieving a predetermine degree of hydrolysis. Other process conditions such as pH also can be adjusted, such as by addition of NaOH, KOH and the like, to obtain the desired degree of hydrolysis. Preferably, hydrolysis proceeds to no more than 30%, more preferably between about 5 to about 15% hydrolysis, and even more preferably, about 10% hydrolysis.

Process conditions, including temperature and pH, are dependent at least in part on the starting material and enzyme used. Typical temperatures for the solution during hydrolysis are between about 10° C. to about 60° C. The pH can be maintained at between about 3 to about 10. More typically, the pH is generally maintained at about neutral, that is, between about 6 to about 8 and more likely between about 6.5 to about 7.5. The protein and enzyme solution also can be stirred during hydrolysis. Generally, pH and temperature are adjusted during hydrolysis, as well as during nanofiltration to obtain the desired process conditions to optimize each process step.

When the desired degree of hydrolysis has been reached, pH, temperature or combinations of both can be utilized to inactivate the enzymes and stop hydrolysis. For example, the solution can be heated to between about 40° C. to about 100° C., more typically between about 75° C. to about 85° C. for at least about 5 minutes or the pH can be adjusted to denature and inactivate the enzymes to terminate protein hydrolysis. Preferably, the enzymes are inactivated prior to nanofiltration.

The hydrolyzed whey protein solution is processed by membrane filtration. It is contemplated that any suitable known membrane filtration process, including but not limited to reverse osmosis, nanofiltration, ultrafiltration and microfiltration, may be used. In one aspect, a nanofiltration process is used. Nanofiltration of the hydrolyzed whey protein solution allows for removal of additional components that may be present in the hydrolysate, thereby enhancing the characteristics of final whey protein product.

Typically, nanofiltration is used to remove minerals and concentrate the final product. It may be desired to remove minerals such as those added during processing to adjust pH. In one aspect, nanofiltration is used to decrease the bitterness of the final whey protein product. Performing the nanofiltration step at elevated temperatures (between at least about 15° C. to about 35° C.) generally will enlarge the pore size of the membrane a sufficient amount so as to be effective for removing additional components such as small peptides and free amino acids. Small peptides are peptides generally between about 2 to about 5 amino acids in length and having molecular weights between about 200 to about 500 daltons. Such peptides are recognized as being very bitter. By removing small peptides through nanofiltration, the bitterness of the final product is reduced.

After nanofiltration, the retentate is collected and dried using any known methods, such as spray drying in a spray tower to obtain a dried whey protein hydrolysate powder having an essentially neutral pH, preferably between about 6 to about 8. The powder typically includes between about 40% to about 100% protein.

The whey protein hydrolysate powder, can be incorporated into solid and liquid food compositions as a source of whey proteins. The whey protein powder also can be blended with unhydrolyzed whey proteins, other protein sources, and other desired ingredients as described herein to provide a whey protein composition suitable for use in preparing solid and liquid food compositions.

EXAMPLES

The following examples are intended to illustrate the invention and not to limit or otherwise restrict the invention.

Example 1

This example demonstrates a process for hydrolyzing a whey protein isolate to provide a whey protein hydrolysate powder that can be incorporated into solid and liquid food compositions.

Provon® 190, a whey protein isolate powder commercially available from Glanbia Nutritionals, Inc. of Twin Falls, Id., is obtained as a liquid prior to spray drying and mixed with water to provide a solution having a solids content of about 17 to about 18% based on the weight of the solution. The solution is heated in a hydrolysis tank to about 45° C. and the pH adjusted with NaOH to about 7.5. An enzyme product, Debitrase® HYW20 commercially available from Rhodia Foods of Madison, Wis., is added in an amount of about 1 pound of enzyme per 100 pounds of protein (or about 1% by weight of the protein). Hydrolysis of the solution is continued for about 2 hours with stirring. The pH is adjusted with NaOH about every 0.5 hours. The hydrolysate is heated to about 75° C. for about 5 minutes to inactivate the enzymes and cooled to about 16-19° C. The product is nanofiltered on a TFC3838SR3-N1 Koch Membrane obtained from Filtration Engineering of Champlin, Minn. Nanofiltration is conducted at a temperature of about 22° C. The solids content of the retentate is about 25%, which is determined using a vacuum oven method for solids determination. The retentate is spray dried on a Niro Tall Form spray dryer from Niro Inc. of Hudson, Wis.

The powder has a pH of about 6.5 to about 7.5, a moisture content of about 2-5% and includes about 86-90% protein, about 1-2% total carbohydrates, about 6-8% ash, and less than about 1% fats, all based on the weight of the powder. The degree of hydrolysis is about 8-12%.

Example 2

This example illustrates the flavor improvement obtained by nanofiltration of a whey protein hydrolysate.

Whey protein solution is hydrolyzed and nanofiltered as described above in Example 1. Four samples of a whey protein hydrolysate solution are separately nanofiltered and analyzed (Batches 1-4). The compositions of nanofiltration feed (hydrolyzed whey protein solution), permeate and retentate for each of the four samples are shown below in Table 1.

TABLE 1

| Batch | Solids (%) | Protein (%) | Ash (%) |
|---|---|---|---|
| 1 | | | |
| Feed | 18 | 12.54 | 0.75 |
| Permeate | 1.88 | 1.51 | 0.15 |
| Retentate | 24.77 | 21.41 | 1.2 |
| 2 | | | |
| Feed | 18 | 12.54 | 0.75 |
| Permeate | 2.35 | 1.98 | 0.17 |
| Retentate | 24.65 | 21.63 | 1.22 |
| 3 | | | |
| Feed | 18 | 12.54 | 0.75 |
| Permeate | 2.31 | 1.96 | 0.15 |
| Retentate | 23.99 | 20.82 | 0.83 |
| 4 | | | |
| Feed | 18 | 12.54 | 0.75 |
| Permeate | 2.76 | 2.34 | 0.2 |
| Retentate | 24.83 | 21.59 | 1.42 |

The permeate is very bitter and contains off flavors for all batches and contains the smaller peptides and components which are the most bitter and have a large impact on flavor. The retentate has a decreased bitter flavor as compared to the permeate.

Example 3

This example demonstrates the stability of a liquid whey protein composition when subjected to heat. Three samples of unhydrolyzed whey protein solution at various pH levels and three samples of hydrolyzed whey protein solution at the same various pH levels are evaluated.

To prepare the protein solution samples, about 50 grams of protein powder is hydrated in water to provide 500 ml of a solution having about 10% solids. The higher solids content (10%) is used to enhance the visibility of the effect of heating on the proteins. The unhydrolyzed whey protein powder is Provon® 190 from Glanbia Nutritionals, Inc. Protein powder obtained according to Example 1 is used as the hydrolyzed whey protein powder. The pH of the solution is adjusted with 85% phosphoric acid as needed to obtain the desired pH. Samples of the solution are placed in glass jars and initial pH and viscosity measured and appearance noted. The samples are heated in the jars in a water bath at about 180° F. and held for about 30 minutes. The jars are removed from the water bath and the samples allowed to cool. Final pH and viscosity are measured and appearance noted. Initial and final conditions of the various samples are presented in Tables 2a and 2b, respectively.

TABLE 2a

|  | Unhydrolyzed Whey Protein | | | Whey Protein Hydrolysate | | |
| --- | --- | --- | --- | --- | --- | --- |
|  | pH as is | pH 4.0 | pH 3.2 | pH as is | pH 4.0 | pH 3.2 |
| pH | 6.39 | 4.02 | 3.2 | 7.28 | 4.0 | 3.2 |
| Viscosity(cP)* | 18 | 17.6 | 17.6 | 16.0 | 34.0 | 16.4 |
| Color | Cloudy | Cloudy | Clear | Cloudy | White | Cloudy |

*Brookfield Spindle #2 at 100 rpm

TABLE 2b

|  | Unhydrolyzed Whey Protein | | | Whey Protein Hydrolysate | | |
| --- | --- | --- | --- | --- | --- | --- |
|  | pH as is | pH 4.0 | pH 3.2 | pH as is | pH 4.0 | pH 3.2 |
| pH | 6.38 | 4.13 | 3.29 | 7.22 | 4.17 | 3.25 |
| Viscosity (cP)* | 15.2 | 61.6 | 84.0 | 14.0 | Partially Gelled | 14.4 |
| Color | White | White | Clear | Slightly cloudy | White, separated | Slightly cloudy |
| Heat Treatment Observations | Fail @ 15 min | Fail @ 10 min | Pass | Pass | Fail @ 5 min | Pass |

*Brookfield Spindle #2 at 100 rpm

Example 4

This example illustrates stability of a neutral pH liquid composition upon heating.

Protein beverages having about 22 grams of protein per 330 milliliters are prepared with formulations that include whey protein products as the sole protein source. One formulation utilizes an untreated whey protein product, as set forth in Table 3, and another formulation utilizes a whey protein product prepared as described in Example 1, as set forth in Table 4. Colorants and flavorings are not included in the beverages to allow for better evaluation of the protein in the beverages.

TABLE 3

| Ingredient | Weight % |
| --- | --- |
| Unhydrolyzed Whey Protein[1] | 7.57 |
| Crystalline Fructose | 7.64 |
| Carrageenan Gum | 0.14 |
| Maltodextrin | 7.87 |
| Water | to 100.0 |

[1]Provon ® 190 Available from Glanbia Nutritionals, Inc., Twin Falls, Idaho

TABLE 4

| Ingredient | Weight % |
| --- | --- |
| Whey Protein Hydrolysate | 8.18 |
| Crystalline Fructose | 7.64 |
| Carrageenan Gum | 0.14 |
| Maltodextrin | 7.87 |
| Water | to 100.0 |

The beverages are prepared by activating carrageenan gum in 200 grams of water by shearing in a blender. The remaining amount of water is mixed with the gum. The protein powders (both treated and untreated) are hydrated in the water and carrageenan gum solution. The solutions are placed in a boiling water bath, heated to about 190° F. and held for about 30 minutes or until gelling occurs. The solutions are removed and cooled. The beverages are characterized before and after heating as set forth in Tables 5a and 5b, respectively.

TABLE 5a

|  | Unhydrolyzed Whey Protein[1] | Whey Protein Hydrolysate Solution |
| --- | --- | --- |
| pH | 6.09 | 7.17 |
| Color | Yellow/Tan | Yellow/Tan |
| Odor | Slight sulfur odor (cooked egg odor) | Dairy, bland |
| Viscosity[2] | 304.4 cp | 97.6 cp |

[1]Provon ® 190 Available from Glanbia Nutritionals, Inc., Twin Falls, Idaho
[2]Brookfield Spindle #2 at 100 rpm TABLE 5b

|  | Unhydrolyzed Whey Protein[1] | Whey Protein Hydrolysate Solution |
| --- | --- | --- |
| pH | 6.15 | 6.86 |
| Color | White | Tan, light flocculation started after about 20 minutes of heating |
| Viscosity[2] | Gelled | 90.5 cp |

[1]Provon ® 190 Available from Glanbia Nutritionals, Inc., Twin Falls, Idaho
[2]Brookfield Spindle #2 at 100 rpm The whey protein hydrolysate is heated until the protein starts to precipitate in order to evaluate the degree of heat stability. Hydrolyzed whey protein begins to precipitate after about 20 minutes of heating. In comparison, an unhydrolyzed whey protein will gel or precipitate after only a few minutes of heating.

Example 5

This example illustrates the heat stability of liquid compositions including hydrolyzed whey proteins. Three samples of unhydrolyzed whey protein solution at various pH levels and three samples of hydrolyzed whey protein solution at the same various pH levels are evaluated.

To prepare the liquid compositions, dry ingredients including protein powder are hydrated in water to provide 500 ml of a solution having about 4% and about 10% solids. The higher solids content (10%) is used to enhance the visibility of the effect of heating on the proteins. The liquid compositions with unhydrolyzed whey protein are set forth in Table 6. The unhydrolyzed whey protein powder is Provon® 190 from Glanbia Nutritionals, Inc. The liquid compositions with hydrolyzed whey protein are set forth in Table 7. Protein powder obtained according to Example 1 is used as the hydrolyzed whey protein powder.

TABLE 6

|  | Sample No. | | | |
| --- | --- | --- | --- | --- |
|  | 1 Weight % | 2 Weight % | 3 Weight % | 4 Weight % |
| Sugar | 8.2 | — | 8.2 | — |
| Sucralose | — | 0.04 | — | 0.04 |
| Erythritol | — | 6 | — | 6 |
| Unhydrolyzed Whey Protein[1] | 4 | 4 | 10 | 10 |
| Canola oil | 1.5 | 1.5 | 1.5 | 1.5 |
| Cellulose gum | 0.4 | 0.4 | 0.4 | 0.4 |

TABLE 6-continued

| | Sample No. | | | |
|---|---|---|---|---|
| | 1 Weight % | 2 Weight % | 3 Weight % | 4 Weight % |
| Flavor | 0.2 | 0.2 | 0.2 | 0.2 |
| Water | 85.69 | 87.85 | 79.69 | 81.85 |
| Color | 0.01 | 0.01 | 0.01 | 0.01 |

[1]Provon ® 190 Available from Glanbia Nutritionals, Inc., Twin Falls, Idaho

TABLE 7

| | Sample No. | | | |
|---|---|---|---|---|
| | 1 Weight % | 2 Weight % | 3 Weight % | 4 Weight % |
| Sugar | 8.2 | — | 8.2 | — |
| Sucralose | — | .04 | — | 0.04 |
| Erythritol | — | 6 | — | 6 |
| Unhydrolyzed Whey Protein | 4 | 4 | 10 | 10 |

TABLE 7-continued

| | Sample No. | | | |
|---|---|---|---|---|
| | 1 Weight % | 2 Weight % | 3 Weight % | 4 Weight % |
| Canola oil | 1.5 | 1.5 | 1.5 | 1.5 |
| Cellulose gum | 0.4 | 0.4 | 0.4 | 0.4 |
| Flavor | 0.2 | 0.2 | 0.2 | 0.2 |
| Water | 85.69 | 87.85 | 79.69 | 81.85 |
| Color | 0.01 | 0.01 | 0.01 | 0.01 |

[1]Provon ® 190 Available from Glanbia Nutritionals, Inc., Twin Falls, Idaho

The remaining ingredients are mixed with the liquid composition. Samples of the solution are placed in glass jars and initial pH and viscosity measured and appearance noted. The samples are heated in the jars in a water bath at about 180° F. and held for about 30 minutes. The jars are removed from the water bath and the samples allowed to cool. Final pH and viscosity are measured and appearance noted. Initial and final conditions of the various samples are presented in Tables 8a and 8b, respectively.

TABLE 8a

| | Unhydrolyzed Whey Protein Solution Sample No.: | | | | Whey Protein Hydrolysate Solution Sample No.: | | | |
|---|---|---|---|---|---|---|---|---|
| | 1 | 2 | 3 | 4 | 1 | 2 | 3 | 4 |
| pH | 6.91 | 6.95 | 6.70 | 6.70 | 7.14 | 7.15 | 7.27 | 7.24 |
| Viscosity (cP)[1] | 16.8 | 16.0 | 23.2 | 21.6 | 15.2 | 14.8 | 20.4 | 18.4 |
| Color | Pale yellow | Pale yellow | Yellow | Yellow | Pale yellow | Pale yellow | Yellow | Yellow |

[1] Brookfield Spindle #2 at 100 rpm.

TABLE 8b

| | Unhydrolyzed Whey Protein Solution Sample No.: | | | | Whey Protein Hydrolysate Solution Sample No.: | | | |
|---|---|---|---|---|---|---|---|---|
| | 1 | 2 | 3 | 4 | 1 | 2 | 3 | 4 |
| pH | 6.89 | 6.90 | 6.80 | 6.86 | 7.13 | 7.20 | 7.23 | 7.22 |
| Viscosity (cP)[1] | Partial gel | Partial gel | Gelled | Gelled | 15.0 | 15.5 | 19.6 | 19.0 |
| Color | White | White | White | White | Pale yellow | Pale yellow | Yellow | Yellow |
| Heat Treatment Observation | Fail | Fail | Fail | Fail | Pass | Pass | Pass | Pass |

[1]Brookfield Spindle #2 at 100 rpm

Example 6

This example demonstrates a protein bar formulation using a hydrolyzed whey protein isolate product prepared according to the process of Example 1 as 100% of the protein source. The bar composition is set forth in Table 9.

TABLE 9

| Ingredient | Weight % | Amount (g) |
| --- | --- | --- |
| Hydrolyzed Whey Protein | 41 | 175 |
| HFCS 55%[1] | 22 | 92.5 |
| Corn Syrup 42/43[2] | 19 | 80.5 |
| Glycerine | 7 | 30 |
| Almond Butter | 5 | 20 |
| Inulin | 5 | 20 |
| Konjac Flour | <1 | 3 |
| Flavor | <1 | 4 |

[1] high fructose corn syrup
[2] dextrose equivalents

The dry ingredients listed above are blended together in a stand mixer. Liquid ingredients and almond butter are mixed together and heated to about 125° F. The liquid mixture is added to the dry ingredients in the stand mixer and mixed into a dough. The dough is rolled out and cut into bars or extruded.

Example 7

This example demonstrates the improved functional characteristics of a first bar prepared using the formulation and procedures of Example 6. A second bar is prepared as a control from a formulation that includes an unhydrolyzed whey protein isolate product as 100% of the protein source using the procedures of Example 6. The bar composition for the second bar is set forth in Table 10. The bar compositions are formed into bars of about 55 grams each.

TABLE 10

| Ingredient | Weight % | Amount (g) |
| --- | --- | --- |
| Unhydrolyzed Whey Protein[1] | 38 | 160 |
| HFCS 55%[2] | 22 | 92.5 |
| Corn Syrup 42/43[3] | 19 | 80.5 |
| Glycerine | 9 | 40 |
| Almond Butter | 6 | 25 |
| Inulin | 5 | 20 |
| Konjac Flour | <1 | 3 |
| Flavor | <1 | 4 |

[1] Provon ® 190 Available from Glanbia Nutritionals, Inc., Twin Falls, Idaho
[2] high fructose corn syrup
[3] dextrose equivalents The bars are allowed to set for 19 days. The bars are analyzed using a TAXT2 Texture Analyzer from Texture Technologics Corp. of Scarsdale, N.Y. The probe used with the texture analyzer is a TA44 craft blade that is used to measure peak force and bar toughness. The speed of the probe as it cuts through the bar is about 1 millimeter per second. The toughness of each bar is analyzed at three locations across the length of the bar.

Figure 4:
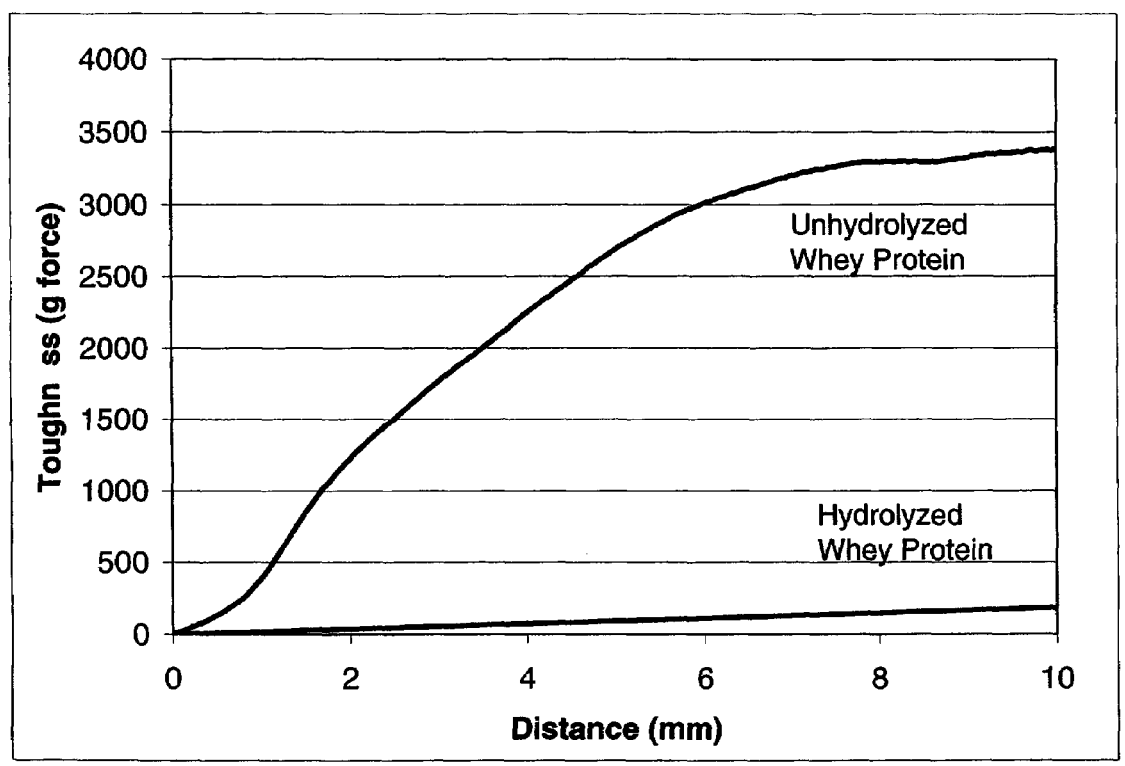
FIG. 4 is a graphical illustration of fracture toughness of a solid food product prepared from compositions in accordance with the present invention.

FIG. 4 illustrates the results obtained from the texture analyzer. As can be seen from FIG. 4, the force required to cut through the first bar (hydrolyzed whey protein) is between about 200 grams, and the force to cut through the second bar (control) is between about 3200 grams to about 3700 grams. Thus, a significantly greater (more than ten-fold) amount of force is required to break through a bar that incorporates an unhydrolyzed whey protein source as compared to a bar that incorporates a whey protein source prepared in accordance with the present invention.

Example 8

This example demonstrates a whey protein composition that includes both hydrolyzed and unhydrolyzed whey proteins.

A whey protein hydrolysate composition prepared as described above in Example 1 is blended with an unhydrolyzed whey protein isolate. Provon® 190, commercially available from Glanbia Nutritionals, Inc., is used as the unhydrolyzed whey protein isolate. The whey protein hydrolysate and Provon® 190 are blended in a ratio of about 65:35, respectively, to provide a partially hydrolyzed whey protein composition with the properties set forth in Table 11.

TABLE 11

| Component | Measurement |
| --- | --- |
| Protein | 87-89% |
| Moisture | 3.0-5.0% |
| Fat | <1.0% |
| Ash | 4.5-6.5 |
| Lactose | 1.0-1.5% |
| pH | 6.5-7.5 |
| Degree of Hydrolysis | 5-8% |

Example 9

This example illustrates protein bar formulations that incorporate various whey protein compositions, including blends of unhydrolyzed whey proteins and whey protein hydrolysates. The dough is prepared as described in Example 6.

The formulation set forth in Table 12 provides 10 grams of whey protein in a 65 gram bar. The protein component includes 70% whey protein hydrolysate and 30% unhydrolyzed whey protein.

TABLE 12

| Ingredient | Weight % |
| --- | --- |
| Rice Flour | 15.6 |
| Hydrolyzed Whey Protein | 10.6 |
| Unhydrolyzed Whey Protein[1] | 4.6 |
| Oat Fiber | 5 |
| Vitamin/Mineral Blend | 1.3 |
| Flavor | 2.2 |
| HFCS 55%[2] | 37.6 |
| Sucralose | <0.01 |
| Xanthan Gum | 0.03 |
| Water | 2 |
| Macadamia Nut Butter | 6 |
| Lecithin | 0.1 |
| Chocolate Coating | 15 |

[1] Provon ® 190 Available from Glanbia Nutritionals, Inc., Twin Falls, Idaho
[2] high fructose corn syrup The formulation set forth in Table 13 provides 10 grams of whey protein in a 65 gram bar. The protein component includes 30% whey protein hydrolysate and 70% unhydrolyzed whey protein.

TABLE 13

| Ingredient | Weight % |
| --- | --- |
| Rice Flour | 15.6 |
| Hydrolyzed Whey Protein | 4.6 |
| Unhydrolyzed Whey Protein[1] | 10.6 |
| Oat Fiber | 5 |
| Vitamin/Mineral Blend | 1.3 |
| Flavor | 2.2 |
| HFCS 55%[2] | 37.6 |
| Sucralose | <0.01 |
| Xanthan Gum | 0.03 |
| Water | 2 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho
[2]high fructose corn syrup The formulation set forth in Table 14 provides 25 grams of whey protein in a 65 gram bar. The protein component includes 70% whey protein hydrolysate and 30% unhydrolyzed whey protein.

TABLE 14

| Ingredient | Weight % |
| --- | --- |
| Hydrolyzed Whey Protein | 25.8 |
| Unhydrolyzed Whey Protein[1] | 11.1 |
| Flavor | 2.2 |
| HFCS 55%[2] | 37.8 |
| Sucralose | <0.01 |
| Xanthan Gum | 0.03 |
| Water | 2 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho
[2]high fructose corn syrup The formulation set forth in Table 15 provides 25 grams of protein in a 65 gram bar. The protein component includes 30% whey protein hydrolysate and 70% unhydrolyzed whey protein.

TABLE 15

| Ingredient | Weight % |
| --- | --- |
| Hydrolyzed Whey Protein | 10.7 |
| Unhydrolyzed Whey Protein[1] | 25 |
| Flavor | 2.2 |
| HFCS 55%[2] | 39.0 |
| Sucralose | <0.01 |
| Xanthan Gum | 0.03 |
| Water | 2 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho
[2]high fructose corn syrup The formulation set forth in Table 16 provides 10 grams of protein in a 65 gram bar. The protein component includes 70% whey protein hydrolysate and 30% unhydrolyzed whey protein.

TABLE 16

| Ingredient | Weight % |
| --- | --- |
| Rice Flour | 14.4 |
| Hydrolyzed Whey Protein | 10.5 |
| Unhydrolyzed Whey Protein[1] | 4.5 |
| Oat Fiber | 3 |
| Vitamin/Mineral Blend | 0.5 |
| Flavor | 2.2 |
| Maltitol Syrup | 38.9 |
| Glycerine | 3.9 |
| Sucralose | <0.01 |
| Xanthan Gum | 0.01 |
| Water | 1 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

The formulation set forth in Table 17 provides 10 grams of protein in a 65 gram bar. The protein component includes 30% whey protein hydrolysate and 70% unhydrolyzed whey protein.

TABLE 17

| Ingredient | Weight % |
| --- | --- |
| Rice Flour | 14.4 |
| Hydrolyzed Whey Protein | 4.5 |
| Unhydrolyzed Whey Protein[1] | 10.5 |
| Oat Fiber | 3 |
| Vitamin/Mineral Blend | 0.5 |
| Flavor | 2.2 |
| Maltitol | 38.9 |
| Glycerine | 3.9 |
| Sucralose | <0.01 |
| Xanthan Gum | 0.01 |
| Water | 1 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

The formulation set forth in Table 18 provides 25 grams of protein in a 65 gram bar. The protein component includes 70% whey protein hydrolysate and 30% unhydrolyzed whey protein.

TABLE 18

| Ingredient | Weight % |
| --- | --- |
| Hydrolyzed Whey Protein | 24.8 |
| Unhydrolyzed Whey Protein[1] | 10.7 |
| Flavor | 2.2 |
| Maltitol Syrup | 35.6 |
| Glycerine | 3.56 |
| Sucralose | <0.01 |
| Xanthan Gum | 0.01 |
| Water | 2 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

The formulation set forth in Table 19 provides 25 grams of protein in a 65 gram bar. The protein component includes 30% whey protein hydrolysate and 70% unhydrolyzed whey protein.

TABLE 19

| Ingredient | Weight % |
| --- | --- |
| Hydrolyzed Whey Protein | 10.7 |
| Unhydrolyzed Whey Protein[1] | 24.9 |
| Flavor | 2.1 |
| Maltitol Syrup | 35.6 |
| Glycerine | 3.6 |
| Sucralose | <0.01 |
| Xanthan Gum | 0.01 |
| Water | 2 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

The formulation set forth in Table 20 provides 20 grams of protein in a 65 gram bar. The protein component includes 50% whey protein hydrolysate and 50% unhydrolyzed whey protein.

TABLE 20

| Ingredient | Weight % |
| --- | --- |
| Hydrolyzed Whey Protein | 16 |
| Unhydrolyzed Whey Protein[1] | 16 |
| Oat Fiber | 2.2 |
| Flavor | 2.1 |
| Maltitol Syrup | 37.8 |
| Glycerine | 3.8 |
| Sucralose | <0.01 |
| Xanthan Gum | 0.01 |
| Water | 1 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

The formulation set forth in Table 21 provides 20 grams of protein in a 65 gram bar. The protein component includes 100% unhydrolyzed whey protein.

TABLE 21

| Ingredient | Weight % |
| --- | --- |
| Unhydrolyzed Whey Protein[1] | 32 |
| Oat Fiber | 2 |
| Flavor | 2.1 |
| Maltitol Syrup | 38 |
| Glycerine | 3.8 |
| Sucralose | <0.01 |
| Xanthan Gum | 0.01 |
| Water | 1 |
| Macadamia Nut Butter | 6 |
| Lecithin | 0.1 |
| Chocolate Coating | 15 |

[1]Provon ® 190 Available from Glanbia Nutritionals, Inc., Twin Falls, Idaho

Example 10

This example demonstrates the improved characteristics of protein bars that incorporate a whey protein composition that includes a blend of hydrolyzed and unhydrolyzed whey proteins as compared to protein bars that incorporate unhydrolyzed whey proteins.

Bars that incorporate whey protein compositions including blends of hydrolyzed and unhydrolyzed whey proteins are prepared from various formulations set forth in Example 9. The bars are prepared as described in Example 6. The bars are placed under accelerated shelf life conditions for two months. The bars are maintained at about 90° F. to accelerate toughening of the bars. One month under the accelerated shelf life conditions simulates approximately three months at regular room temperature. Bar toughness is measured using a texture analyzer as described in Example 7 and is monitored over the two-month period.

Figure 5:
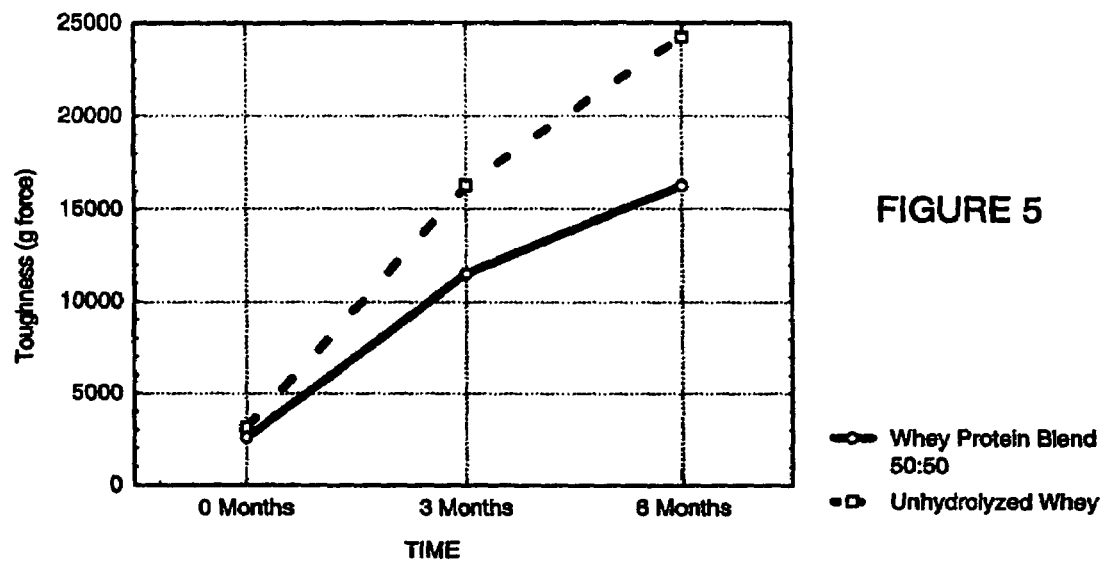
FIG. 5 is a graphical illustration of fracture toughness over an extended period of time of solid food products prepared from compositions in accordance with the present invention.
Figure 6:
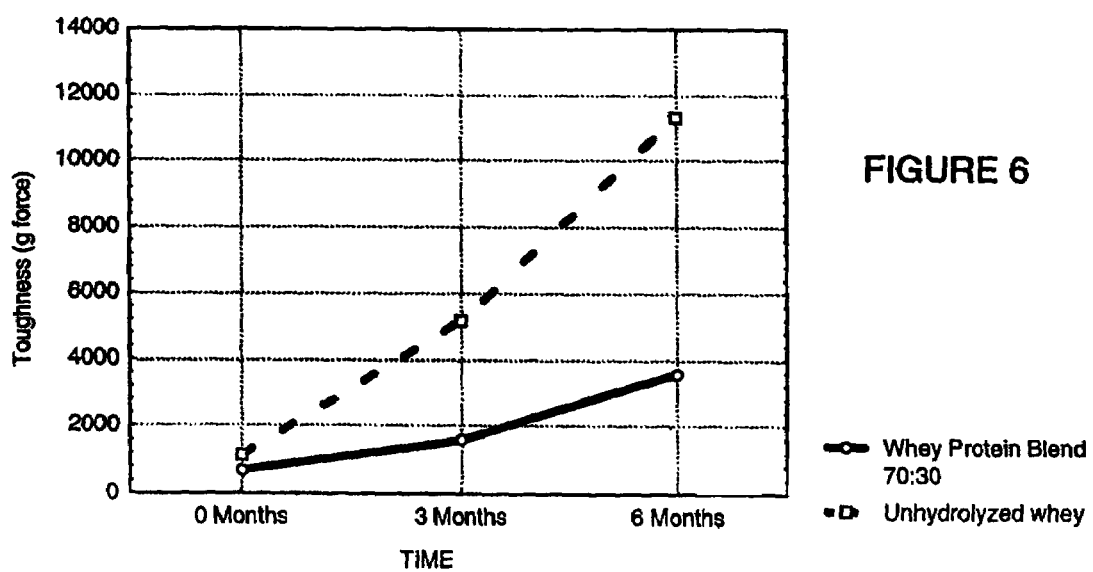
FIG. 6 is a graphical illustration of fracture toughness over an extended period of time of solid food products prepared from compositions in accordance with the present invention.

FIG. 5 illustrates the averaged results obtained from the texture analyzer for bars having a 50:50 blend of hydrolyzed and unhydrolyzed whey proteins (Table 20 of Example 9), as well as for controls bars incorporating unhydrolyzed whey proteins only (Table 10 of Example 7). FIG. 6 illustrates the averaged results obtained from the texture analyzer for bars having a 70:30 blend of hydrolyzed and unhydrolyzed whey proteins, respectively, (Tables 12, 14, 16 and 18 of Example 9) as well as for controls bars incorporating unhydrolyzed whey proteins only (Table 10 and 21 of Examples 7 and 9).

Many modifications and variations may be made in the techniques and compositions described and illustrated herein without departing from the spirit and scope of the present invention. Accordingly, the techniques and compositions described and illustrated herein should be understood to be illustrative only and not limiting upon the scope of the present invention.

What is claimed is:

1. An edible food product having improved shelf life comprising, in combination:
a protein source component including a mixture of powdered hydrolyzed whey protein and, optionally, unhydrolyzed protein, said hydrolyzed protein consisting of at least about 50% by weight of the protein source component, said hydrolyzed protein processed by hydrolyzing whey protein in water maintained at a pH in the range of about 6.0 to 8.0 in combination with a proteolytic enzyme, said enzyme subsequently rendered inactive and said hydrolyzed protein filtered at a temperature in the range of about 15° C. to 35° C. to effect removal of free amino acids and peptides generally about 2 to 5 amino acids in length and having molecular weight between about 200 to 500 daltons with a retentate of solids content; and an edible food composition component comprising no more than about 98% by weight of said food product.

2. The food product of claim 1 wherein the food product is characterized by at least about 40 weight percent protein based on the weight of the food product.

3. The food product of claim 1 wherein the food product is characterized by at least about 45 weight percent protein based on the weight of the food product.

4. The food product of claim 1 wherein the protein component includes between about 20 to about 50 weight percent unhydrolyzed protein based on the weight of the food product.

5. The food product of claim 1 wherein the hydrolyzed whey protein is derived from whey, whey protein concentrate, whey protein isolate, and combinations thereof.

6. The food product of claim 1 wherein the solid food product is a protein bar.

7. The food product of claim 1 wherein said whey protein is not denatured.

* * * * *